United States Patent [19]

Earl et al.

[11] 4,338,216

[45] Jul. 6, 1982

[54] STABILIZATION OF AQUEOUS TERTIARY DI-β-HYDROXY AMINE OXIDES

[75] Inventors: Gary W. Earl, Bexley; Howard M. Hickman, Worthington, both of Ohio

[73] Assignee: Sherex Chemical Company, Inc., Dublin, Ohio

[21] Appl. No.: 106,747

[22] Filed: Dec. 26, 1979

[51] Int. Cl.$^3$ .................. B01J 13/00; B01F 17/16; C11D 1/75

[52] U.S. Cl. .................. 252/311; 252/61; 252/307; 252/357; 252/547; 252/DIG. 13; 252/DIG. 14

[58] Field of Search .................. 252/311, 547, 357

[56] References Cited

U.S. PATENT DOCUMENTS 3,332,999  7/1967  Mitchell et al. .................. 252/547 X
3,928,249  12/1975  Nunziata et al. .................. 252/547 X Primary Examiner—Richard D. Lovering
Attorney, Agent, or Firm—Mueller and Smith

[57] ABSTRACT

Disclosed is a method for stabilizing an aqueous tertiary di-(β-hydroxy organo) amine oxide which comprises incorporating therein a stabilizing proportion of an amine oxide salt which is the reaction product of a tertiary amine oxide and a protic acid.

26 Claims, No Drawings

STABILIZATION OF AQUEOUS TERTIARY DI-β-HYDROXY AMINE OXIDES

BACKGROUND OF THE INVENTION

The present invention relates to aqueous tertiary di-β-hydroxy amine oxides and particularly to their stabilization against phase separation.

Wieland [Ber., 54, 2353 (1921)] first proposed the oxidation of tertiary amines with hydrogen peroxide. He assumed that the hydrogen peroxide added first to the amine to form an ammonium peroxide compound which then decomposed to amine oxide and water. This intermediate ammonium peroxide complex formation has been substantially by Oswald et al [J. Org. Chem., 28, 657 (1963)]. Trialkylaminehydrogen peroxide adducts have been isolated from reactions using 90+% $H_2O_2$ at low temperatures (e.g. $-50°$ C.). These complexes are unstable, colorless liquids at room temperature and have been shown by infrared spectroscopy to be hydrogen bonded polar complexes. These complexes are thermally unstable and decompose to yield trialkylamine oxides and water. This decomposition is quite rapid at 50° C.

The most obvious method for the direct oxidation of tertiary amines is to use concentrated hydrogen peroxide sans solvent. However, Hoh et al [J.A.O.C.S., 40, 268 (1963)] has shown that oxidation of dimethyldodecylamine without added solvent at 60° C. using 90% $H_2O_2$ proceeds only to 40% completion in 3 hours reaction time. With 70% aqueous $H_2O_2$ at 50° C., a 45% completion was realized in 3 hours; however, the completion leveled off at 60% oxide in 10 hours reaction time. Using 35% aqueous hydrogen peroxide, the reaction proceeds more rapidly to yield 50% amine oxide in less than 2 hours reaction time and about 85% amine oxide at the completion of the reaction.

The preferred method determined by Hoh et al was the addition of 35% aqueous hydrogen peroxide to the tertiary amine with stirring at 60° C. over a 1 hour period during which time the mixture became gelatinous. Sufficient water was added to keep the reaction mixture fluid. Upon completion of peroxide addition, the proportion of water required to yield a 30%–40% amine oxide solution was added and the temperature was raised to 75° C. A conversion approaching 100% then was realized in 2 hours reaction time. The incremental addition of water was found to give rapid oxidation initially and a quick completion of the reaction. Alternatively, when all of the water was added at the commencement of the reaction, the initial rate of reaction was slow and excessive reaction times were experienced. Hoh et al determined that the optimum reaction temperature for their reaction procedure was about 60°–65° C. They noted that at higher temperatures some decomposition apparently occurred (a yellow color developed) and at lower temperatures the reaction rate decreased. Present day commercial manufacturing of aqueous tertiary amine oxides typically involves the incremental addition of aqueous hydrogen peroxide to the tertiary amine and water.

Aqueous trialkyl, ether dialkyl and polyoxyalkylene amine oxides (e.g. 35%–50% amine oxide solids) appear to provide stable, one phase systems upon storage. However, it has been determined that aqueous tertiary di-β-hydroxy amine oxides are not storage stable but split into two layers upon standing. Many of these hydroxy amine oxides cannot be produced by the noted oxidation reaction without added aqueous solvent and are hygroscopic so that removal of water therefrom is difficult if not impossible. Thus, a great need exists for stabilizing such aqueous amine oxide systems.

BROAD STATEMENT OF THE INVENTION

One aspect of the present invention is a method for stabilizing an aqueous tertiary di-(β-hydroxy organo) amine oxide. This method comprises incorporating therein a stabilizing proportion of an amine oxide salt which is the reaction product of a tertiary amine oxide and a proton-donating (protic) acid. Another aspect of the present invention is the resulting stabilized aqueous tertiary amine oxide product.

Advantages of the present invention include the ability to provide a storage-stable aqueous tertitary di-(β-hydroxy organo) amine oxide. Another advantage of the present invention is that such stabilization can be accomplished very effectively and efficiently. These and other advantages will become readily from the disclosure herein.

DETAILED DESCRIPTION OF THE INVENTION

A variety of systems are included within the purview of the present invention. Clearly, the probable most efficient and economic system is a self-stabilizing system wherein protic acid is added to the aqueous β-hydroxy amine oxide. Alternatively, a different β-hydroxy amine oxide reacted with protic acid may be incorporated into the aqueous amine oxide for its stabilization. Another alternative is to add a totally different protonated amine oxide to the blend for its stabilization. Of course, combinations of the foregoing are included in the present invention also. It must be recognized that depending upon the desired end use of the stabilized aqueous amine oxide, stabilizers chemically dissimilar from the amine oxide to be stabilized may not be desirable.

The amine oxide required to be stabilized is a tertiary di-(β-hydroxy organo) amine oxide. Such amine oxide may be represented conventionally by the following general structure:

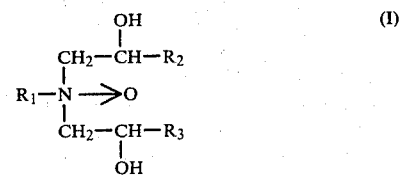

In structure I, $R_1$ is a linear or branched, substituted or unsubstituted, saturated or unsaturated aliphatic, alicyclic-aliphatic, or aliphatic-aromatic group, optionally containing linkages of ether, amine, amide, or sulfide. Advantageously, $R_1$ is a $C_1$–$C_{22}$ alkyl group or $C_1$–$C_{22}$ alkyl ether group. Preferable $R_1$ groups include linear or branched aliphatic groups of 8–20 carbon atoms and alkyl ether groups of the following general structure:

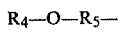

where, $R_4$ is a $C_8$–$C_{22}$ aliphatic group and $R_5$ is a $C_2$–$C_4$ polymethylene group. Preferably, $R_4$ is a linear or branched $C_{12}$–$C_{15}$ aliphatic group and $R_5$ is a trimethylene group. Broadly, $R_2$ and $R_3$ can be hydrogen or an organic group. Though not necessary, it is distinctly preferred that $R_2$ and $R_3$ be the same group. Advantageous $R_2$ and $R_3$ groups include hydrogen and $C_1$–$C_{20}$ alkyl groups optionally containing linkages of ether. Preferably, $R_2$ and $R_3$ each is a hydrogen, a methyl group, or an ethyl group. Additional preferred $R_2$ and $R_3$ groups can be found in applicants' commonly assigned copending application Ser. No. 06/106,746, filed Dec. 26, 1979, now U.S. Pat. No. 4,275,236, entitled "Tertiary Di-(β-Hydroxy Organo) Amine Oxides and Their Preparation", the disclosure of which is expressly incorporated herein by reference. Note that the amine oxides disclosed therein are stable in anhydrous form but not when dispersed in water, though the addition of a protic acid provides stability to them in water.

As mentioned above, the preferred stabilizer for use in the present invention is a portion of the β-hydroxy amine oxide which is desired to be stabilized and which has been reacted with a protic acid. Broadly, though, the amine oxide of the stabilizing amine oxide salt can be virtually any amine oxide. Thus, the substituents of the amine oxide (attached to the nitrogen of the amine oxide nucleus) can be a linear or branched, substituted or unsubstituted, saturated or unsaturated aliphatic, alicyclic-aliphatic, or aliphatic-aromatic group, optionally containing linkages of ether, amine, amide, or sulfide. Advantageous substituents of the amide oxide are alkyl groups, alkyl ether groups, alkyl sulfide groups, alkyl amide groups, polyoxyalkylene groups, all optionally bearing a hydroxyl group and/or containing light methyl (lower alkyl) substitution. Preferred broad amine oxides are trialkyl amine oxides, (β-alkoxy alkyl) dialkyl amine oxides, dialkyl polyoxyalkylene amine oxides, and alkyl di(polyoxyalkylene) amine oxides. Preferably, though, the amine oxide of the stabilizing amine oxide salt is an alkyl or alkylether di-(β-hydroxy organo) amine oxide for improved compatibility of the amine oxide to be stabilized with the stabilizing amine oxide salt, especially for ultimate use of the product.

The preferred and simplest way for forming the stabilizing aqueous tertiary amine oxide blend is to merely add a protic acid to the aqueous tertiary di-(β-hydroxy organo) amine oxide in a proportion to protonate (or neutralize) at least about 10% of the tertiary amine oxide contained in the blend. Note also that the tertiary amine may be neutralized prior to the tertiary amine oxide formation and a stabilized tertiary amine oxide blend still is provided. When an amine oxide stabilizing salt derived from a dissimilar amine oxide is to be used, such amine oxide desirably is protonated and then added to the aqueous tertiary amine oxide in a proportion of at least about 10% by weight of the ultimate blend being formed. Suitable protic acids include, for example, HCl, $H_2SO_4$, acetic acid, lactic acid, $HNO_3$, citric acid, phosphoric acid, and the like and mixtures thereof. It should be mentioned that the neutralized (protonated) amine oxide may be used as a heel in the oxidation reaction of the tertiary amine used in making the amine oxides. Further schemes will be readily apparent to the skilled artisan.

Generally, the stabilized aqueous tertiary amine oxide blend will be composed of between about 10% and 70% β-hydroxy amine oxide, between about 10% and 40% stabilizing amine oxide salt, and between about 20% and 80% water with the proportion of β-hydroxy amine oxide preferably being equal to or greater than the proportion of the stabilizing amine oxide salt. For the preferred stabilized tertiary amine oxide blend wherein the β-hydroxy amine oxide to be stabilized merely is protonated, the proportion of amine oxide generally ranges from between about 0% and 70%, the proportion of stabilizing β-hydroxy amine oxide salt between about 10% and 80%, and the proportion of water between about 20% and 80% by weight. In such blend the total proportion of amine oxide and stabilizing amine oxide salt should range from between about 20% and 80% by weight. For such preferred blend it may be preferred on occasion to protonate or neutralize the entire β-hydroxy amine oxide content for ensuring excellent long term stability of the blend including freeze-thaw stability and heat stability thereof.

While the precise mechanism responsible for the stability of the aqueous tertiary amine oxide blend is not fully understood, it is theorized that the stabilizing amine oxide salt may be acting as a cationic surfactant in the blend for its stabilization. Alternatively, it has been theorized that the β-hydroxy amine oxide has a structure conducive for forming an intermolecular double six-membered hydrogen bonded system. The addition of the protic acid, then, may merely break such hydroxy bonds to convert the oxygen atom of the oxide group to a hydroxyl group which with the other two hydroxyl groups participate in solubilizing the amine oxide in the water of the blend. Regardless of the precise mechanism explaining the stability of the novel stabilized aqueous tertiary amine oxide blends, the method for achieving such stabilization has been amply tested and determined as disclosed herein.

The novel stabilized aqueous tertiary amine oxide blend finds wide use as a wetting agent, surfactant, or dispersant. Accordingly, the novel amine oxide blend may be used as a foaming agent or foam stabilizer in shampoos or liquid diswashing detergents, as froth stabilizers in the froth flotation of mineral ores (e.g. the froth flotation of sylvite from sylvinite), and similar uses. Additionally, certain of the tertiary amine oxides have been determined to be effective as a foam stabilizer for stabilizing a foam of alkylbenzene sulfonate foaming agent as shown in Examples II–IV, inclusive of commonly assigned patent application of Egan and Watts, U.S. Ser. No. 06/052,665, filed June 27, 1979, and entitled "Amine Oxide Foam Stabilizers for Alkylbenzene Sulfonate Foaming Agents", now U.S. Pat. No. 4,263,177, the disclosure of which is expressed incorporated herein by reference.

The following examples show how the present invention can be practiced but should not be construed as limiting. In this application, all proportions and percentages are by weight and all units are in the metric system, unless otherwise expressly indicated.

EXAMPLE I

The amine oxide used in this example was VAROX 185E amine oxide (supplied by Sherex Chemical Company, Dublin, Ohio, VAROX being their trademark) which has the formula:

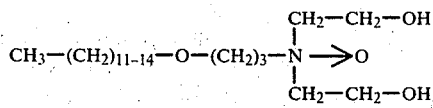

The specifications for all samples of the VAROX 185E amine oxides used are: 39%–43% amine oxide solids, 0.1–0.5% residual $H_2O_2$, pH 8.0–8.8, 0.5% maximum free amine, Gardner color of 1 maximum, clear and bright systems, and average molecular weight range of 379–393. Samples of the pH 8.0–8.8 amine oxide split into layers upon standing, thus showing their instability. As a comparison, three different samples of the amine oxide were brought to pH 11 by the addition of 50% aqueous NaOH. After 18 hours storage time, all three samples had separated into two layers.

Next, several samples of the amine oxide were brought to a pH of 5.5–6.5 by the addition of a variety of protic acids. The analyses of the neutralized aqueous amine oxides is displayed in Table I.

TABLE I

| Sample No. | % Tertiary Amine Oxide | Acid Used | Final pH | Color (Gardner) | % Total Amine Oxide | % Free Amine | % $H_2O_2$ Residual |
|---|---|---|---|---|---|---|---|
| 3551-194 | 98.7 | 3N HCl | 6.0 | 1+ | 31.3 | — | 0.25 |
| 3551-195 | 99.5 | 3N HCl | 6.0 | 1 | 36.6 | — | 0.41 |
| 3551-196 | 99.3 | 3N HCl | 6.2 | 1 | 40.8 | — | 0.44 |
| 3673-8 | 99.5 | 3N HCl | 6.9 | 1 | 37.6 | — | 0.64 |
| 3673-10a | 99.5 | Citric | 5.5 | 1 | 39.0 | — | 0.45 |
| 3673-10b | 99.5 | Con HCl | 5.4 | 1 | 35.5 | — | 0.35 |
| 3673-10c | 99.5 | 70% $H_2SO_4$ | 5.0 | 1 | 33.9 | 0.6 | 0.50 |

The 3673-8 sample was neutralized before oxidation of the tertiary amine to form the amine oxide, while all remaining samples were neutralized after amine oxide formation. All acidified samples were clear and bright also.

All samples were subjected to freeze-thaw stability tests by freezing the samples overnight (about 14–20 hours) followed by thawing them at ambient indoor temperature (about 0.5 hours). This procedure then was repeated for all samples. Following the second thawing, all samples remained stable, one-phase, clear and bright systems. Additionally, portions of the last four samples in Table I were frozen for 2 months and then thawed. Each sample still remained stable, one-phase, clear and bright systems having a Gardner color of 1 upon their thawing.

Other portions of the last four samples in Table I additionally were placed in an oven held at 45.55° C. (105° F.) in order to evaluate their heat stability. After 7 days and 30 days heat storage time, all samples remained stable, one-phase, clear and bright systems. After 60 days, only then did the samples begin to thinly split (Gardner color of 2–3 for all samples). Thus, the acidified aqueous amine oxides are remarkably heat stable also. Note, that it is unlikely that the aqueous amine oxides would be subjected to more than 2 or 3 weeks of such heat before their use commercially.

Still, portions of the first three samples in Table I were placed in an oven held at 54.55° C. (130° F.), a temperature far higher than the commercial products should encounter. After 24 hours time, sample 3551-194 had split and after 5 days the sample had severely split (Gardner color of 4). After 24 hours, sample 3551-195 split slightly but returned to a one-phase system upon cooling, and after 5 days this sample split heavily (Gardner color of 2). However, sample 3551-196 remained a stable, one-phase, clear and bright system after 24 hours and 5 days with a Gardner color of 2 after 5 days time. Again, unexpected stability is demonstrated by the stabilized aqueous amine oxides of the present invention.

EXAMPLE II

The amine oxide used in this example can be represented by

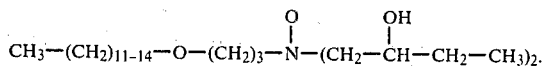

This amine oxide was made by adding 50% aqueous $H_2O_2$ to the corresponding tertiary amine (approximate MW of 275–289) in water at about 70° C. to make a 40% solids amine oxide product having a pH of 8.

A sample of the pH 8 aqueous amine oxide split into two layers upon standing overnight at ambient indoor temperature. Separation and analysis of both layers revealed that the top layer contained 89% amine oxide and 0.84% free amine, while the bottom layer contained only 39% amine oxide and 0.84% free amine.

Another sample of the same pH 8 aqueous amine oxide was pH adjusted to 5.5 with HCl to produce a clear and brilliant system having a Gardner color of 2. The acidified aqueous amine oxide was stored at ambient indoor temperature for 5 months and still remained a clear and bright, one-phase product.

To further characterize the protic acid addition to obtain phase stability of amine oxides, aliquots of different samples of the un-neutralized amine oxide were titrated in both isopropyl alcohol (IPA) or $H_2O$/IPA (equal weight proportions). Titration curves revealed that at the equivalence point, 1.0 equivalent of the HCl is consumed by 1.0 equivalent of the amine oxide. In IPA the equivalence point is pH 2.3 and in IPA/$H_2O$ it is 3.0. For the preferred pH range of 5.5–6.5 for the aqueous amine oxide, the titration data additionally show the following.

| pH | % Protonated Amine Oxide | |
| | IPA | $H_2O$/IPA |
|---|---|---|
| 5.5 | 45 | 36 |
| 6.5 | 14 | 21 |

Thus, the preference for requiring at least about 10% neutralized (protonate) amine oxide for providing a stable, one-phase amine oxide product.

EXAMPLE III

The amine oxide tested has the following structure:

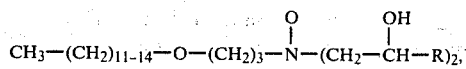

where 75% of R is H and 25% of R is $CH_3$. This amine oxide was prepared by the oxidation of the corresponding tertiary amine (MW=370–390) with 1.1 eq. of 50% aqueous $H_2O_2$ at 60° C. to make a 40% solids amine oxide having a pH of 8.8.

A sample of the pH 8.8 amine oxide split into two layers and was very hazy after standing overnight. Another sample was neutralized with concentrated HCl to pH 5.5. This sample remains a crystal clear one phase product. A further sample was blended with a neutralized dimethyl lauryl amine oxide (30% aqueous solution resulting from the addition of HCl to the dimethyl lauryl amine oxide to obtain a pH of 3). About 10% by weight of the dimethyl lauryl amine oxide.HCl solution was added to bring the pH of the hydroxy amine oxide to below 6.5. The resulting stabilized amine oxide product was clear and especially brilliant with no phase separation.

It should be noted that the dimethyl lauryl amine oxide exhibited a sharp inflection point at pH 3.0 when the titration curve with concentrated HCl was plotted. Calculations reveal that at pH 3.0, one equivalent of the amine oxide had been reacted with one equivalent of HCl.

The foregoing results demonstrate several aspects of the present invention. One aspect is that a mixture of β-hydroxy amine oxides can be stabilized against phase separation by the addition of acid. Another aspect is that a stabilized amine oxide, even of much different structure, can stabilize a β-hydroxy amine oxide at relatively low concentrations and apparently with no compatibility problems between the two amine oxides. While the precise mechanism for this method of stabilization is not fully understood, it certainly is demonstrated to work remarkably well in this example.

EXAMPLE IV

The amine oxide evaluated is represented by the following structure:

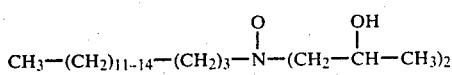

This amine oxide was made by oxidizing the corresponding tertiary amine (MW = 391–405) with 1.1 eq. of 50% aqueous $H_2O$ at 60° C. to produce a 40% solids system having a pH of 8.

An aliquot of the pH 8 aqueous amine oxide split and became cloudy after standing for 14 days. Another aliquot was neutralized with HCl to pH 5.5 to make a clear, one-phase system. A further aliquot was blended with 10% of weight of the HCl neutralized dimethyl lauryl amine oxide of Example III to yield a pH 6.5 one-phase system which was clear and especially brilliant.

Again, the present invention is demonstrated.

EXAMPLE V

Varox 185E amine oxide of Example I (100 gram aliquot) was blended with the dimethyl lauryl amine oxide.HCl adduct (10 gm.) of Example III. The resulting product became a clear, one-phase solution. This system is clearer and more brilliant than the $H_2SO_4$ neutralized system reported as sample no. 3673-10c in Example I.

We claim:

1. A method for stabilizing an aqueous tertiary di-(β-hydroxy organo) amine oxide blend, comprising between 10% and 70% by weight of a tertiary di (β-hydroxy organo) amine oxide, and between 20% and 80% by weight water which splits into layers upon standing, which method comprises incorporating therein a stabilizing proportion of an amine oxide salt which is the reaction product of a tertiary amine oxide and a protic acid, provided that when the tertiary amine oxide of the salt is the same as the tertiary amine oxide of the blend, then the tertiary amine oxide of the stabilized blend is between 0% and 70% by weight of said blend.

2. The method of claim 1 wherein said stabilizing proportion of said amine oxide salt is at least about 10% by weight of said blend.

3. The method of claim 1 wherein said tertiary di-(β-hydroxy organo) amine oxide and tertiary amine oxide of said amine oxide salt are the same.

4. The method of claim 3 wherein said amine oxide salt is incorporated by the addition of said protic acid to said aqueous blend.

5. The method of claim 1 or 4 wherein said tertiary di-(β-hydroxy organo) amine oxide can be represented by

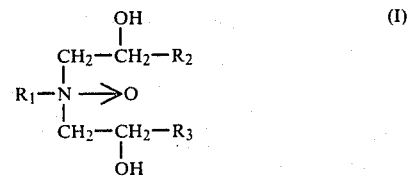

where, $R_1$ is a linear or branched, substituted or unsubstituted, saturated or unsaturated aliphatic, alicyclic, or aliphatic-aromatic group, optionally containing linkages of ether, amine, amide, or sulfide; and $R_2$, $R_3$, each, are H or an organic group.

6. The method of claim 5 wherein $R_1$ is a $C_1$–$C_{22}$ alkyl or alkyl ether group, and $R_2$, $R_3$, each, are H or a $C_1$–$C_{20}$ alkyl or alkyl ether group.

7. The method of claim 6 wherein $R_1$ is

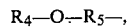

where $R_4$ is a linear or branched $C_4$–$C_{22}$ aliphatic group and $R_5$ is a $C_2$–$C_4$ polymethylene group.

8. The method of claim 6 wherein $R_2$ and $R_3$ are the same, and are H or a $C_1$–$C_2$ alkyl group.

9. The method of claim 4 wherein the proportion of protic acid is adequate to substantially fully protonate all of said tertiary di-(β-hydroxy organo) amine oxide.

10. The method of claim 3 wherein said incorporating is by the addition of said protic acid to an aqueous tertiary di-(β-hydroxy organo) amine followed by oxidation of said tertiary amine to form said stabilized amine oxide blend.

11. The method of claim 1 wherein said tertiary amine of said stabilizing amine oxide salt contains substituents selected from the groups consisting of alkyl groups, alkyl ether groups, alkyl sulfide groups, alkyl amide groups, and polyoxyalkylene groups.

12. The method of claim 1, 4, or 10 wherein said protic acid is selected from the group consisting of HCl, $H_2SO_4$, acetic acid, lactic acid, formic acid, $HNO_3$, citric acid, phosphoric acid, and mixtures thereof.

13. The method of claim 1 wherein said blend contains by weight between about 10% and 70% of said tertiary di-(β-hydroxy organo) amine oxide, between about 10% and 40% of said amine oxide salt, and between about 20% and 80% of water.

14. The method of claim 4 wherein said blend contains by weight between about 0% and 70% of said tertiary di-(β-hydroxy organo) amine oxide, between about 10% and 80% of said tertiary amine oxide salt, and between about 20% and 80% of water, provided that the total proportion of amine oxide and amine oxide salt is between about 20% and 80%.

15. A stabilized aqueous tertiary amine oxide blend consisting essentially of:

(a) between 10% and 70% by weight of a tertiary di-(β-hydroxy organo) amine oxide;

(b) a stabilizing proportion of an amine oxide salt which is the reaction product of a tertiary amine oxide and a protic acid; and (c) between 20% and 80% by weight of water, provided that when the tertiary amine oxide of said salt (b) is the same tertiary amine oxide of (a), then said amine oxide (a) is between 0% and 70% by weight of said blend.

16. The stabilized blend of claim 15 wherein said stabilizing proportion of said amine oxide salt is at least about 10% by weight of said blend.

17. The stabilized blend of claim 15 wherein said tertiary di-(β-hydroxy organo) amine oxide and tertiary amine oxide of said amine oxide salt are the same.

18. The stabilized blend of claim 15 or 17 wherein said tertiary di-(β-hydroxy organo) amine oxide can be represented by

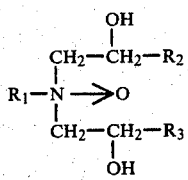 (I)

where, $R_1$ is a linear or branched, substituted or unsubstituted, saturated or unsaturated aliphatic, alicyclic, or aliphatic-aromatic group, optionally containing linkages of ether, amine, amide, or sulfide; and $R_2$, $R_3$, each, are H or an organic group.

19. The stabilized blend of claim 18 wherein $R_1$ is a $C_1$–$C_{22}$ alkyl or alkyl ether group, and $R_2$, $R_3$, each, are H or a $C_1$–$C_{20}$ alkyl or alkyl ether group.

20. The stabilized blend of claim 19 wherein $R_1$ is

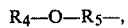

where $R_4$ is a linear or branched $C_4$–$C_{22}$ aliphatic group and $R_5$ is a $C_2$–$C_4$ polymethylene group.

21. The stabilized blend of claim 19 wherein $R_2$ and $R_3$ are the same, and are H or a $C_1$–$C_2$ alkyl group.

22. The stabilized blend of claim 17 wherein the proportion of protic acid is adequate to substantially fully protonate all of said tertiary di-(β-hydroxy organo) amine oxide.

23. The stabilized blend of claim 15 wherein said tertiary amine of said stabilizing amine oxide salt contains substituents selected from the group consisting of alkyl groups, alkyl ether groups, alkyl sulfide groups, alkylamide groups, and polyoxyalkylene groups.

24. The stabilized blend of claim 15 or 17 wherein said protic acid is selected from the group consisting of HCl, $H_2SO_4$, acetic acid, lactic acid, formic acid, $HNO_3$, citric acid, phosphoric acid, and mixtures thereof.

25. The stabilized blend of claim 15 wherein said blend contains by weight between about 10% and 70% of said tertiary di-(β-hydroxy organo) amine oxide, between about 10% and 40% of said amine oxide salt, and between about 20% and 80% of water.

26. The stabilized blend of claim 17 wherein said blend contains by weight between about 0% and 70% of said tertiary di-(β-hydroxy organo) amine oxide, between about 10% and 80% of said tertiary amine oxide salt, and between about 20% and 80% of water, provided that the total proportion of amine oxide and amine oxide salt is between about 20% and 80%.

* * * * *